(12) United States Patent
Chancellor et al.

(10) Patent No.: US 9,744,267 B2
(45) Date of Patent: *Aug. 29, 2017

(54) RAPID PREPARATION OF STEM CELL MATRICES FOR USE IN TISSUE AND ORGAN TREATMENT AND REPAIR

(71) Applicant: University of Pittsburgh—Of the Commonwealth System of Higher Education, Pittsburgh, PA (US)

(72) Inventors: Michael B. Chancellor, Pittsburgh, PA (US); Johnny Huard, Houston, TX (US); Christopher C. Capelli, Houston, TX (US); Steve Chung, Pittsburgh, PA (US); Michael S. Sacks, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/972,402

(22) Filed: Dec. 17, 2015

(65) Prior Publication Data

US 2016/0101217 A1 Apr. 14, 2016

Related U.S. Application Data

(60) Continuation of application No. 14/322,092, filed on Jul. 2, 2014, now abandoned, which is a continuation of application No. 13/046,120, filed on Mar. 11, 2011, now Pat. No. 8,790,680, which is a division of application No. 11/138,168, filed on May 25, 2005, now Pat. No. 7,906,110, which is a division of application No. 10/081,835, filed on Feb. 22, 2002, now abandoned.

(60) Provisional application No. 60/271,267, filed on Feb. 23, 2001.

(51) Int. Cl.
| | |
|---|---|
| *A01N 63/00* | (2006.01) |
| *A61L 27/38* | (2006.01) |
| *A61L 27/36* | (2006.01) |
| *C12N 5/00* | (2006.01) |
| *C12N 5/077* | (2010.01) |
| *C12N 5/0775* | (2010.01) |
| *A61L 27/22* | (2006.01) |
| *C12N 5/071* | (2010.01) |
| *A61K 35/12* | (2015.01) |

(52) U.S. Cl.
CPC ......... *A61L 27/3834* (2013.01); *A61L 27/225* (2013.01); *A61L 27/3629* (2013.01); *A61L 27/3679* (2013.01); *C12N 5/0068* (2013.01); *C12N 5/0658* (2013.01); *C12N 5/0668* (2013.01); *C12N 5/0697* (2013.01); *A61K 35/12* (2013.01); *A61L 2430/22* (2013.01); *C12N 2533/56* (2013.01); *C12N 2533/74* (2013.01); *C12N 2533/90* (2013.01); *C12N 2533/92* (2013.01)

(58) Field of Classification Search
None
See application file for complete search history.

(56) References Cited

U.S. PATENT DOCUMENTS

| | | | | |
|---|---|---|---|---|
| 5,223,241 | A * | 6/1993 | Isobe | A61K 51/1027 424/1.53 |
| 6,171,340 | B1 * | 1/2001 | McDowell | A61F 2/30724 623/18.11 |
| 7,771,717 | B2 * | 8/2010 | Badylak | A61K 35/38 424/93.7 |
| 8,790,680 | B2 * | 7/2014 | Chancellor | A61L 27/3629 424/422 |

FOREIGN PATENT DOCUMENTS

WO  WO 99/56785 A3 * 11/1999 ............. A61K 35/34

* cited by examiner

*Primary Examiner* — Janice Li
(74) *Attorney, Agent, or Firm* — Goodwin Procter LLP (57) ABSTRACT

A rapid method for preparing stem cell and physiologically acceptable matrix compositions for use in tissue and organ repair is described. Compared with previous tissue engineering materials, the stem cell-matrix compositions of the present invention do not require long-term incubation or cultivation in vitro prior to use in in vivo applications. The stem cells can be from numerous sources and may be homogeneous, heterogeneous, autologous, and/or allogeneic in the matrix material. The stem cell-matrix compositions provide point of service utility for the practitioner, wherein the stem cells and matrix can be combined not long before use, thereby alleviating costly and lengthy manufacturing procedures. In addition, the stem cells offer unique structural properties to the matrix composition which improves outcome and healing after use. Use of stem cells obtained from muscle affords contractility to the matrix composition.

14 Claims, 2 Drawing Sheets

RAPID PREPARATION OF STEM CELL MATRICES FOR USE IN TISSUE AND ORGAN TREATMENT AND REPAIR

RELATED APPLICATIONS

This application is a continuation of U.S. application Ser. No. 14/322,092 (now abandoned), filed on Jul. 2, 2014, which is a continuation of U.S. application Ser. No. 13/046,120, filed on Mar. 11, 2011 (now U.S. Pat. No. 8,790,680), which is a divisional of U.S. application Ser. No. 11/138,168, filed on May 25, 2005 (now U.S. Pat. No. 7,906,110), which is a divisional of U.S. application Ser. No. 10/081,835, filed on Feb. 22, 2002 (now abandoned), which claims the benefit of provisional U.S. Application No. 60/271,267, filed on Feb. 23, 2001, the contents of which are hereby incorporated by reference in their entireties.

This invention was made with Government support under Grant No. DK55387 awarded by the National Institutes of Health. The Government has certain rights in this invention.

FIELD OF THE INVENTION

The present invention generally relates to cellular-based tissue engineering and methods of preparing cell and biologically compatible matrix combinations. More specifically, the invention relates to muscle-derived stem cell-based matrix compositions and products and to a rapid method of producing and utilizing such compositions and products at a tissue or organ site of need.

BACKGROUND OF THE INVENTION

Presently, all attempts at cellular-based tissue engineering are being done at the manufacturing site where uniform and continuous infiltration of cells into a matrix are prepared together before shipping for implantation. The manufacturing of cellular based medical devices is costly and time consuming. Part of the lengthy time consumption results from the necessity of incubating the cells in the matrix for long periods before in vivo use. For example, in the overview of a company involved in the preparation of cell scaffolds, it is stated that "after [the cells] develop over a period of a few weeks, the cells on the scaffold are kept under optimal conditions in bioreactors. The bioreactors are challenging to build because they have to create perfect conditions to grow the implants." (Advanced Tissue Sciences, Inc., La Jolla, Calif.).

It is known that cellular tissue engineering requires continuous biological devices that are pre-constructed prior to implantation (L. Germain et al., 2000, *Medical & Biological Engineering & Computing*, 38(2):232-40; W. W. Minuth et al., 1998, *Cell Tissue Res.*, 291(1):1-11; G. K. Naughton et al., 1999, *Clin. in Plastic Surgery*, 26(4):579-86, viii). Until the present time using the invention described herein, most cell-matrices were made using non-stem cells. However, these cells have proven to be difficult to work with (F. Berthod and O. Damour, 1997, *British Journal of Dermatology*, 136:809-816). In order to produce such non-stem cell matrices, prolonged incubation times are needed after the cells have been incorporated into the matrix. As a particular example, it has been reported that at least 3 to 5 hours of incubation time is needed for fibroblasts to attach to a scaffold and another 2 to 3 weeks of incubation time is required to achieve confluence (J. F. Hansbrough et al., 1991, *Surgery*, 111(4):438-446). Moreover, the use of collagen sponges requires that the cells have to be incubated in the sponge for at least 24 hours, and another 8 to 10 days are needed for the cells to achieve confluence (F. Berthod et al., 1993, *Biomaterials*, 14(10): 749-754).

In addition, currently available cell-matrices require careful monitoring. Cells on scaffolds are vigorously tested to confirm and maintain the proper metabolic rate that will allow the cells on scaffolds to grow and reproduce in a steady-state manner resulting in optimal materials (Advanced Tissue Sciences, Inc. La Jolla, Calif.).

For cell matrix products used in wound coverage, there has been a perpetual belief that uniform layers of continuous cells are needed for a functional product (F. A. Auger et al., 1988, *Med. Biol. Eng. Compu.*, 36: 801-812; S. T. Boyce, 1996, *Tissue Eng.*, 2: 255-266; O. Damour, et al., 1997, "Cultured autologous epidermis for massive burn wounds: 15 years of practice". Rouabhia, M. (Ed.): *Skin substitute production by tissue engineering: clinical and fundamental applications*. Landes, Austin, pp. 23-45). As an example, the importance of continuous layers has been emphasized in conjunction with the marketing of the product Apligraf® (Organogenesis, Inc., Canton, Mass.), which is carefully cultured on scaffold in a bilayer for over 20 days to produce a continuous cell layer of dermis and epidermis.

Current methods of producing cell matrices for in vivo tissue and organ repair are very costly and time consuming. Such cell matrices are costly due to the specialized factories and/or procedures needed to produce these products. Also, since cell-matrix products involve living biological cells/tissue, a tremendous loss of product occurs from shipping, the delays associated therewith, and the like. Additionally, given the nature of the products, obtaining regulatory approval for new products that are based on living cells and a new matrix poses difficulties.

Thus, there is a serious need for cell-matrix compositions that are low in cost, that are versatile, and easily prepared and/or manufactured. There is a further need for cell matrix compositions that do not require extensive in vitro incubation or cultivation periods after the cells have been incorporated into the matrix. Those in the art have recognized that a major problem remaining to be solved is the delay in producing the cell-matrix product after initial preparation. Specifically, it has been stated that there is a problem of a three week delay necessary to produce a sufficient amount of autologous keratinocytes and fibroblasts for the production of reconstructed skin. (F. Berthod and O. Damour, 1997, *British Journal of Dermatology*, 136: 809-816). The present invention provides a solution for the above-mentioned problems and delays currently extant in the art.

SUMMARY OF THE INVENTION

One aspect of the present invention provides methods of preparing stem cell matrices, particularly biomatrices, for use in tissue and organ repair. In accordance with the present invention, stem cells are employed rather than other cell types (e.g., differentiated or non-stem cells). In addition, the stem cells and the matrix material are admixed or combined shortly before or immediately prior to use, thereby eliminating the need for long-term incubations or culture of cells with matrix material. Thus, the methods are rapid and allow the preparation of a stem cell-based biomatrix material as needed.

In another aspect of this invention, the stem cell-biomatrix material can be in the form of a sling, patch, wrap, such as are employed in surgeries to correct, strengthen, or otherwise repair tissues and organs in need of such treatment. As is appreciated by the person skilled in the art, a sling can comprise a material placed beneath deficient sphincter to provide support, e.g., a pubvaginal sling to repair stress urinary incontinence. A patch can comprise a material that is applied over a section of weak, thin, or deficient organ or tissue that is either solid or hollow, e.g., a tissue engineering patch of heart or bladder. A wrap refers to a circumferential patch, e.g., a material placed around a blood vessel or gastroesophageal sphincter.

Another aspect of the present invention provides stem cell-matrix compositions for in vivo tissue and/or organ repair, or surgical or wound healing, that can be produced at the "point-of-service", i.e., at the bedside or surgical suite just before the medical procedure for tissue and/or organ treatment or repair occurs. According to this invention, prolonged delays (as well as increased costs) resulting from commercial preparation of a cell matrix material are alleviated.

Yet another aspect of the present invention provides stem cell-biological, physiologically compatible adhesive (i.e., bioadhesive) and/or biological matrix (i.e., biomatrix) combinations, or compositions thereof, for direct application to the external surface of organs such as skeletal muscle and skin, and smooth muscle, such as the diaphragm, bladder, intestine and heart. In addition, these combinations, or compositions thereof, can be applied to organs such as the liver, spleen, thymus, spinal cord and bone. In accordance with the present invention, the stem cells or progenitor cells can be autologous (obtained from the recipient, including humans) or allogeneic (obtained from a host source other than the recipient, including humans).

A further aspect of the present invention provides an implantable, innervatable physiologically acceptable three-dimensional scaffolding for tissue and organ repair comprising a preparation of stem cells and a physiologically acceptable biological substrate, preferably small intestine submucosa (SIS). Preferably, the stem cells are obtained from muscle. In accordance with the present invention, the stem cell-biomatrix material, or stem cell-three-dimensional scaffolding, as described herein, are capable of contractility, particularly when the stem cells employed are obtained from muscle.

Additional aspects, features and advantages afforded by the present invention will be apparent from the detailed description and exemplification hereinbelow.

DESCRIPTION OF THE FIGURES

FIG. 2 presents results of experiments performed to test the contractility of muscle stem cells incorporated into a SIS scaffold. (Example 9). As observed in FIG. 2, none of the SIS strips at any time point up to 8-weeks showed any contractile activity. In the 8-week of MDSC/SIS preparations, spontaneous contractile activity was observed cultures (8 of 8 specimens). Also, in 8-week MDSC/SIS preparations, the frequency and amplitude of spontaneous contractile activity were decreased by the addition of 20 µM succinylcholine.

DETAILED DESCRIPTION OF THE INVENTION

The present invention involves methods of preparing stem cell or progenitor cell matrices for use in tissue and organ repair, comprising a medically- or physiologically-acceptable matrix material and autologous and/or allogeneic stem cells, preferably, muscle-derived stem cells. The invention involves admixing, such as by inoculating or seeding the stem cells into the medically- or physiologically-acceptable matrix material and using the combined stem cell-matrix composition or product almost immediately for in vivo tissue or organ treatment and repair.

According to this invention, the stem cell matrices are made for in vivo use in tissue or organ treatment and repair without the need for prolonged, prior in vitro incubation of the stem cell matrices after the cells have been inoculated or introduced into a given biomatrix. Unlike the present invention, previous cell matrices made for in vivo tissue or organ repair have depended on a prolonged incubation of the cells in the matrix prior to use. By using stem cells in the stem cell matrix compositions of this invention, rather than non-stem cells, or other types of cells, the need for prolonged in vitro incubation is not required.

As a result of the present invention, methods of producing stem cell-matrix compositions that can be used almost immediately after preparation at the time of use are now possible. This is important because stem cell-matrix compositions provided for in vivo tissue and/or organ treatment or repair can be produced at the "point-of-service", i.e., at the bedside or surgical suite just before the medical procedure for tissue and/or organ treatment or repair occurs. Prolonged delays (as well as increased costs) resulting from sending cells to an outside laboratory for incorporation and incubation into a matrix, and then waiting for several weeks to receive the cell-matrix material for medical use (e.g., for in vivo tissue or organ treatment or repair procedures) are obviated and avoided in view of the present invention.

In accordance with the present invention, a short duration mixture of stem cells on a scaffold with non-uniform or irregular coverage of cells, on and/or within the scaffold, results in the proliferation of stem cells in and on the matrix to result in cellular differentiation, the release of factors by the stem cells, and improved outcome. Although it was at first believed that uniform and continuous layers of cells, as well as long periods of careful incubation or culturing, were needed to produce cell-based matrix compositions, it was surprisingly discovered that the use of stem cells at the point of service resulted in the proliferation of stem cells in the matrix that yielded smooth layers and improved healing of the biological device. It was further discovered that point of service application of stem cells with a biologic device, e.g., a biological matrix, improved function. For example, the stem cells were capable of releasing factors that allowed improved therapy, treatment and overall function.

According to the present invention, the stem cells can be mixed with the matrix material in vitro not long before application to a tissue or organ site in vivo. Alternatively, the stem cells can be mixed with, or inoculated onto, the matrix material just at the time of use. In some cases, depending upon cell source, cell concentration and matrix material, the admixing of stem cells and matrix material, or the inoculation of stem cells onto matrix material, needs no more time than the time that it takes to combine the stem cells and the matrix at the point of use.

In accordance with the present invention, the in vitro incubation of stem cells with matrix material is performed for from about 5 seconds to less than about 12 hours, preferably for from about 5 seconds to about 30 minutes. The in vitro incubation of stem cells with matrix material according to this invention is generally less than about 3 hours, preferably, less than about 1 hour, more preferably, less than about 30 minutes. Indeed, the experiments described herein indicate that use of the stem cells and matrix material combination can be used virtually immediately after stem cells are mixed with or inoculated onto a biomatrix. No long-term (e.g., >about 12 hours, days, or weeks) of incubation or culture time is necessary to achieve results using the combination of stem cell-matrix material (i.e., stem cell-matrix material composition) in a variety of applications. Such stem cell-matrix combinations and compositions can be used in wound healing; surgical procedures; the sealing of openings, fissures, incisions, and the like; and the augmentation, filling, or reconstitution of tissues and organs of the body, for example, following surgery, or as the result of diseases, disorders, conditions, accidents, or therapies.

The compositions of the invention can be used in treatments for diseases such as impaired muscle contractility of the heart, diaphragm, gastrointestinal tract, and genitourinary tract. Use of the present invention is also made for a variety of treatments, repair, augmentation, filling and healing of skin (dermis and epidermis) and soft tissue, muscle, bone, ligaments, and the like, so as to reduce scarring that results from conventional techniques.

A variety of biological or synthetic solid matrix materials (i.e., solid support matrices, biological adhesives or dressings, and biological/medical scaffolds) are suitable for use in this invention. The matrix material is preferably medically acceptable for use in in vivo applications. Nonlimiting examples of such medically acceptable and/or biologically or physiologically acceptable or compatible materials include, but are not limited to, solid matrix materials that are absorbable and/or non-absorbable, such as small intestine submucosa (SIS), e.g., porcine-derived (and other SIS sources); crosslinked or non-crosslinked alginate, hydrocolloid, foams, collagen gel, collagen sponge, polyglycolic acid (PGA) mesh, polyglactin (PGL) mesh, fleeces, foam dressing, bioadhesives (e.g., fibrin glue and fibrin gel) and dead de-epidermized skin equivalents in one or more layers. As an exemplary bioadhesive, fibrin glue preparations have been described in WO 93/05067 to Baxter International, Inc., WO 92/13495 to Fibratek, Inc. WO 91/09641 to Cryolife, Inc., and U.S. Pat. Nos. 5,607,694 and 5,631,019 to G. Marx.

In an embodiment of the present invention, the stem cell-biomatrix material can be in the form of a sling, patch, wrap, such as are employed in surgeries to correct, strengthen, or otherwise repair tissues and organs in need of such treatment. As is appreciated by the person skilled in the art, a sling can comprise a material placed beneath deficient sphincter to provide support, e.g., a pubvaginal sling to repair stress urinary incontinence. A patch can comprise a material that is applied over a section of weak, thin, or deficient organ or tissue that is either solid or hollow, e.g., a tissue engineering patch of heart or bladder. A wrap refers to a circumferential patch, e.g., a material placed around a blood vessel or gastroesophageal sphincter.

The stem cells or progenitor cells can be autologous (obtained from the recipient, including humans) or allogeneic (obtained from a donor source other than the recipient, including humans). For allogeneic stem cell or progenitor cell sources, the closest possible immunological match between donor and recipient is desired. If an autologous source is not available or warranted, donor and recipient Class I and Class II histocompatibility antigens can be analyzed to determine the closest match available. This minimizes or eliminates immune rejection and reduces the need for immunosuppressive or immunomodulatory therapy. If required, immunosuppressive or immunomodulatory therapy can be started before, during, and/or after the matrix is applied or introduced into a patient. For example, cyclosporin A, or other immunosuppressive drugs, can be administered to the recipient. Immunological tolerance may also be induced prior to transplantation by alternative methods known in the art (D. J. Watt et al., 1984, *Clin. Exp. Immunol.* 55:419; D. Faustman et al., 1991, *Science* 252: 1701).

According to the present invention, stem cells or progenitor cells are prepared, isolated or obtained from a variety of sources. For example, the stem cells or progenitor cells may be from bone marrow or from muscle (e.g., skeletal muscle). Preferred are muscle-derived stem cells (MDSC), also called muscle stem cells (MSC) herein, which have been isolated as described in WO 99/56785 (University of Pittsburgh) and in U.S. Pat. No. 6,866,842 and U.S. Pat. No. 7,115,417 to M. Chancellor et al., the contents of which are hereby incorporated by reference herein in their entireties.

The stem cells utilized in the stem cell matrix compositions can be combinations of different types of stem cells, e.g., heterogeneous populations of stem cells obtained from autologous or allogeneic donor sources, or they can be homogeneous stem cell populations (from autologous or allogeneic sources). Combinations of stem cells of different origins (e.g., a combination of bone marrow and muscle stem cells) are also envisioned. The stem cells can be obtained from animal tissues, including human tissue, such as muscle, adipose, liver, heart, lung and the nervous system, as non-limiting examples. In addition, the tissues may be adult, fetal, or embryonic tissues.

The stem cell-bioadhesive or biomatrix combinations, or compositions thereof, can be directly applied to the external surface of organs such as skin, skeletal muscle and smooth muscle, e.g., the diaphragm, bladder, intestine and heart. In addition, these combinations, or compositions thereof, can be applied to organs such as the liver, spleen, thymus, spinal cord and bone.

In addition, the stem cells can be genetically modified to contain an expression vector, e.g., plasmid or viral, containing one or more heterologous genes which are expressed and whose expression products are produced at the site at which the stem cell-matrix is applied or introduced in vivo. Accordingly, the cells may be genetically engineered to contain one or more nucleic acid sequence(s) encoding one or more active biomolecules, and to express these biomolecules, including proteins, polypeptides, peptides, hormones, metabolites, drugs, enzymes, and the like. The stem cell-matrix composition or product can serve as a long-term local delivery system for a variety of treatments, for example, for the treatment of various diseases and pathologies, such as cancer, tissue regeneration and reconstitution, and to deliver a gene product, such as a therapeutic agent, e.g., hormone or factor, to a tissue or organ site.

The stem cells may be genetically engineered by a variety of molecular techniques and methods known to those having skill in the art, for example, transfection, infection, transduction, or direct DNA injection. Transduction as used herein commonly refers to cells that have been genetically engineered to contain a foreign or heterologous gene via the introduction of a viral or non-viral vector into the cells. Viral vectors are preferred. Transfection more commonly refers to cells that have been genetically engineered to contain a foreign gene harbored in a plasmid, or non-viral vector. The stem cells can be transfected or transduced by different vectors and thus can serve as gene delivery vehicles to allow the gene products to be expressed and produced at the tissue or organ site.

Although viral vectors are preferred, those having skill in the art will appreciate that the genetic engineering of cells to contain nucleic acid sequences encoding desired proteins or polypeptides, cytokines, and the like, may be carried out by methods known in the art, for example, as described in U.S. Pat. No. 5,538,722, including fusion, transfection, lipofection mediated by precipitation with DEAE-Dextran (Gopal, 1985) or calcium phosphate (Graham and Van Der Eb, 1973, *Virology*, 52:456-467; Chen and Okayama, 1987, *Mol. Cell. Biol.* 7:2745-2752; Rippe et al., 1990, *Mol. Cell. Biol.*, 10:689-695); gene bombardment using high velocity microprojectiles (Yang et al., 1990, *Proc. Natl. Acad. Sci. USA*, 87:9568-9572); microinjection (Harland and Weintraub, 1985, *J. Cell Biol.*, 101:1094-1099); electroporation (Tur-Kaspa et al., 1986, *Mol. Cell. Biol.*, 6:716-718; Potter et al., 1984, *Proc. Natl. Acad. Sci. USA*, 81:7161-7165); DNA (vector)-loaded liposomes (Fraley et al., 1979, *Proc. Natl. Acad. Sci. USA*, 76:3348-3352); lipofectamine-DNA complexes; cell sonication (Fechheimer et al., 1987, *Proc. Natl. Acad. Sci. USA*, 84:8463-8467); receptor-mediated transfection (Wu and Wu, 1987, *J. Biol. Chem.*, 262:4429-4432; Wu and Wu, 1988, *Biochemistry*, 27:887-892); and the like.

Preferred viral vectors are typically derived from non-cytopathic eukaryotic viruses in which non-essential genes have been replaced with the nucleic acid sequence(s) of interest. Non-cytopathic viruses include retroviruses, which replicate by reverse transcription of genomic viral RNA into DNA with subsequent proviral integration into host cellular DNA. Retroviruses have been approved for human gene therapy trials. In general, the retroviruses are replication-deficient, i.e., capable of directing synthesis of the desired proteins, but incapable of manufacturing an infectious particle. Retroviruses from which the retroviral plasmid vectors may be derived include, but are not limited to, Moloney murine leukemia virus, spleen necrosis virus, retroviruses such as Rous sarcoma virus, Harvey sarcoma virus, avian leukosis virus, gibbon ape leukemia virus, human immunodeficiency virus, adenovirus, myeloproliferative sarcoma virus, and mammary tumor virus. In general, the retroviruses used to create a viral vector are preferably debilitated or mutated in some respect to prevent disease transmission.

Standard protocols for producing replication-deficient retroviruses, including the steps of 1) incorporating exogenous genetic material into a plasmid, 2) transfecting a packaging cell line with plasmid, production of recombinant retroviruses by the packaging cell line, 3) collecting viral particles from tissue culture media, and 4) infecting the target cells with viral particles, are provided in M. Kriegler, 1990, "Gene Transfer and Expression, A Laboratory Manual," W. H. Freeman Co., NY; and E. J. Murry, Ed., 1991, "Methods in Molecular Biology," vol. 7, Humana Press, Inc., Clifton, N.J.

Expression vectors containing all the necessary elements for expression are commercially available and known to those skilled in the art. See, e.g., Sambrook et al., 1989, *Molecular Cloning: A Laboratory Manual*, Second Edition, Cold Spring Harbor Laboratory Press, Cold Spring Harbor, N.Y.; F. M. Ausubel et al. (eds), 1995, *Current Protocols in Molecular Biology*, John Wiley & Sons, Inc., New York, N.Y.; D. N. Glover (ed), 1985, *DNA Cloning: A Practical Approach, Volumes I and II*; M. L. Gait (ed), 1984, *Oligonucleotide Synthesis*; Hames and Higgins (eds), 1985, *Nucleic Acid Hybridization*; Hames and Higgins (eds), 1984, *Transcription and Translation*; R. I. Freshney (ed), 1986, *Animal Cell Culture; Immobilized Cells and Enzymes*, 1986, (IRL Press); Perbal, 1984, *A Practical Guide to Molecular Cloning; The Series*, Methods in Enzymology, Academic Press, Inc.; J. H. Miller and M. P. Calos (eds), 1987, *Gene Transfer Vectors for Mammalian Cells*, Cold Spring Harbor Laboratory; Wu and Grossman (eds), *Methods in Enzymology*, Vol. 154; Wu (ed), *Methods in Enzymology*, Vol. 155.

Illustrative examples of vehicles or vector constructs for transfection or infection of the stem cells of the present invention include replication-defective viral vectors, DNA virus or RNA virus (retrovirus) vectors, such as adenovirus, herpes simplex virus and adeno-associated viral vectors. Preferred are adenovirus vectors.

Such vectors will include one or more promoters for expressing the bioactive molecule. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs herein above described); the β-actin promoter; and human growth hormone promoters. The promoter also may be the native promoter that controls the nucleic acid sequence encoding the polypeptide.

The vectors are typically substantially free of any prokaryotic DNA and may comprise a number of different functional nucleic acid sequences. Examples of such functional sequences include nucleic acid, e.g., DNA or RNA, sequences comprising transcriptional and translational initiation and termination regulatory sequences, including promoters (e.g., strong promoters, inducible promoters, and the like) and enhancers which are active in esophagus or small intestine cells. Also included as part of the functional sequences is an open reading frame (nucleic acid sequence) encoding a protein, polypeptide, or peptide of interest. Flanking sequences may also be included for site-directed integration. In some situations, the 5'-flanking sequence will allow for homologous recombination, thus changing the nature of the transcriptional initiation region, so as to provide for inducible or noninducible transcription to increase or decrease the level of transcription, as an example.

In general, the nucleic acid sequence desired to be expressed by the stem cell in the biological matrix is that of a structural gene, or a functional fragment, segment or portion of the gene, which is heterologous to the cell serving as delivery vehicle and which encodes a desired protein or polypeptide product. The encoded and expressed product may be intracellular, i.e., retained in the cytoplasm, nucleus, or an organelle of a cell, or may be secreted by the cell. For secretion, the natural signal sequence present in the structural gene may be retained, or a signal sequence that is not naturally present in the structural gene may be used. When the polypeptide or peptide is a fragment of a protein that is larger, a signal sequence may be provided so that, upon secretion and processing at the processing site, the desired protein will have the natural sequence. Examples of genes of interest for use in accordance with the present invention include genes encoding cell growth factors, suppressor molecules, cell differentiation factors, cell signaling factors and programmed cell death factors.

Preferably, a marker is present for the selection of cells containing the vector construct. The marker may be an inducible or non-inducible gene and will generally allow for positive selection under induction, or without induction, respectively. Examples of commonly used marker genes include neomycin, dihydrofolate reductase, glutamine synthetase, and the like. The vector employed also generally includes an origin of replication and other genes that are necessary for replication in the host cells, as routinely employed by those having skill in the art. As an example, the replication system comprising the origin of replication and any proteins associated with replication encoded by a particular virus may be included as part of the construct.

The replication system is preferably selected so that the gene(s) encode products that are necessary for replication, but do not ultimately transform the stem cells. Such replication systems are represented by replication-defective adenovirus constructed as described, for example, by G. Acsadi et al., 1994, *Hum. Mol. Genet.* 3:579-584, and by Epstein-Barr virus. Examples of replication defective vectors, particularly, retroviral vectors that are replication defective, are described by Price et al., 1987, *Proc. Natl. Acad. Sci. USA*, 84:156; and Sanes et al., 1986, *EMBO J.*, 5:3133.

It will be understood that the final gene construct may contain one or more genes of interest, for example, a gene encoding a bioactive metabolic molecule or a gene encoding a suppressor molecule, such as p53. In addition, cDNA, synthetically produced DNA or chromosomal DNA may be employed utilizing methods and protocols known and practiced by those having skill in the art. A vector may be transduced into the cells through any means known in the art. Non-limiting methods include electroporation, liposomes, and calcium phosphate precipitation. In one alternative, the retroviral or plasmid vector can be encapsulated into a liposome, or coupled to a lipid, and then introduced into a cell. The cells are preferably engineered to contain a plasmid or viral vector in an ex vivo approach.

The stem cells can be admixed with, or introduced into, the biologically compatible matrix by a number of methods known to those having skill in the art. For example, inoculation can be used if the matrix comprises a solid or semi-solid material that does not readily mix with cells in suspension. As another example, a suspension of the stem cells can mixed with a suitable biological or synthetic adhesive (bioadhesive) matrix and the combination can be spread, sprayed, painted, or otherwise applied onto a tissue or organ site where the stem cell matrix forms, e.g., by gelling or solidifying in situ. Accordingly, the stem cell-biomatrix combination may be applied by spreading, painting or coating using a spreading or coating means, such as a small brush, spatula, knife, or other device suitable for medically coating a surface, such as a tissue or organ surface. In addition, compressed air may be used to spray or foam a stem cell-biomatrix mixture or suspension onto a wound or biological surface.

In a further aspect of the invention, the stem cells are attached to, introduced into, or applied to a biomatrix using another type of biomatrix material, for example, a biological adhesive (bioadhesive), such as, but not limited to, fibrin glues or gels. Some bioadhesives and fibrin glues can be photoactivated, or activated by temperature or calcium and are also suitable for use. Further, from about $2.5 \times 10^3$ to about $1 \times 10^6$, preferably about $5 \times 10^3$ to about $1 \times 10^6$ stem cells can be used for admixing with, inoculating, seeding, or otherwise introducing onto or into, the medically or physiologically acceptable matrix material. Preferably, about $1 \times 10^5$ stem cells are deposited per 1 cm$^2$ of matrix material.

In an embodiment of the present invention, a unique processing of stem cells with a biological adhesive and unique application for stem cell tissue engineering are provided. A significant limitation of present tissue engineering approaches, especially heart and blood vessel tissue engineering, is the need for either systemic vascular injection of cells or direct needle inoculation of specific sites in the heart. Each of the aforementioned procedures has significant disadvantages. According to the present invention, a method is provided which allows the attachment of stem cells to the external surface of the target organ, as exemplified and described in the examples herein. Thus, the invention overcomes the limitations that currently exist for heart and blood vessel tissue engineering procedures.

In another embodiment, the stem cell and biologic matrix composition can be applied through a minimally invasive fiberoptic scope (e.g., laparoscope) to multiple sites including, but not limited to, bone, cartilage, ligaments. spinal cord, brain, heart, lung, kidney, digestive and genitourinary organs. For stem cell tissue engineering, muscle stem cells (MSC) and bioadhesive, or biomatrix material, are applied, for example, through a laparoscope to spray or coat kidney or ureter surgical anastomoses to enhance healing and prevent stricture. As another example, a combination of MSC and bioadhesive, or biomatrix material, are applied via orthopedic endoscopy to coat the outside of damaged or weakened bone or disc to promote and/or improve healing and strength, and/or to prevent degeneration. Also encompassed in this embodiment are specifically engineered stem cells which can deliver the expression products of genes encoding bone factors or growth factors at the site during the treatment, repair, or healing process.

Rapid methods of preparing a stem cell matrix for use in tissue and organ treatment and repair are embodied by the present invention. In one aspect, a method of the present invention involves admixing a stem cell preparation with a physiologically acceptable matrix material to form a stem cell matrix and incubating the stem-cell matrix in vitro for about 5 seconds to less than about 12 hours prior to use in the tissues or organs of a recipient. In this method, any suitable physiologically acceptable matrix material can be used, e.g., alginate, fibrin glue, fibrin gel, small intestine submucosa (SIS).

In another aspect, a method of the present invention involves admixing a stem cell preparation with a first physiologically acceptable matrix material to form a first stem cell-matrix combination; introducing the first stem cell-matrix combination onto a second physiologically acceptable matrix material to form a second stem cell-matrix material, wherein the first stem cell-matrix combination and the second physiologically acceptable matrix material are incubated in vitro for between about 5 seconds to less than 12 hours; and applying the second stem cell-matrix material on or in a tissue or organ site in a recipient. In this method, the first medically acceptable matrix material is preferably a bioadhesive such as fibrin glue or gel. The stem cell-fibrin glue biomatrix is then applied to a second medically acceptable biomatrix material, e.g., SIS and the like. (Example 3). A preparation or suspension of stem cells can be simultaneously applied with the bioadhesive material to the second medically acceptable biomatrix material, such as via a syringe, and then spread, or allowed to coat this material, which is then used to treat a tissue or organ site. Alternatively, the stem cells and the bioadhesive material can be mixed together and then the stem cell-bioadhesive mixture can be applied to the second matrix material.

The present invention also provides methods which are not likely to be hampered by the usual regulatory barriers. There is a need for a cost effective combination therapy comprising medical devices and cellular therapy. Keeping the medical devices and stem cells separate until combined at the point of service (e.g., bedside or site of use) provides the solution to the need. A significant advantage of the present invention is moving biological stem cell tissue engineering out of the site of commercial manufacture, e.g., the factory, to the point of service, where the stem cell-matrix product is prepared and used "on location".

The stem cell-biological matrix product according to the present invention is rapidly prepared just before, or at the time of, use. There is no requirement for the cells and the matrix material to be incubated or cultured for long durations, e.g., days or weeks, prior to application or introduction at the tissue or organ site by the practitioner. In addition, the stem cell-matrix material, after combination, allows new structures to form, which was unexpected. The stem cells in the biomatrix combination can change the biomechanical properties of the biological scaffold and create new 2-dimensional and 3-dimensional tissue, muscle and organ structures. For example, muscle stem cells were shown to seed porcine small intestine submucosa (SIS) at the point of service so as to improve the SIS tissue properties (Example 2), for vascular intervention. The stem cells seeding the biological or synthetic matrix afford advantages to the use of the present invention for numerous surgical and treatment procedures.

In accordance with the present invention, muscle stem cells can be added onto a scaffold, which has been demonstrated to behave in a manner similar to that of muscle, providing innervation with neuromuscular receptors. (Examples 8-10). Thus, the present invention allows 3-dimensional muscle repair to a variety of tissues and organs, e.g., sphincters, including the urethra, gastroesophageal sphincter, anal sphincter, as well as wrap and patch including the bladder, intestine and stomach, blood vessels and heart, diaphragm, tendons, muscle and ligaments, thereby extending the advantages of the invention to include not only the tissue engineering of an MSC/SIS patch, for tissue repair, for example, but also the engineering of 3-dimensional repair scaffolding utilizing muscle stem cells

EXAMPLES

The examples described below are provided to illustrate the present invention and are not included for the purpose of limiting the invention.

Example 1

Muscle Stem Cell/Alqinate Dressing Composition

Muscle stem cells (MSC) were harvested from rat hindleg muscle using the pre-plate technique (see WO 99/56785). After obtaining a late plate (i.e., post PP5, preferably, PP6) cell population, 100,000 cells, transduced with a retrovirus vector containing LacZ, were then suspended in 200 microliters of Hank's Buffered Salt Solution (HBSS; Gibco BRL, Grand Island, N.Y.) for use. A 1 cm$^2$ piece of Alginate (Johnson & Johnson Medical, Arlington, Tex.) was cut, dipped into the MSC suspension to prepare the Alginate+MSC composition and immediately placed on a 1 cm$^2$ full-thickness wound defect on the upper dorsum of rat. After 1 week, the completely healed wound was harvested and stained. The results demonstrated that the Alginate+MSC healed with better cosmesis than did Alginate alone. After a week's time, the wound was completely covered with normal skin. Upon histological examination, the Alginate+MSC, showed better wound closure with areas of fibrosis within the deeper wound. In addition, at the dermal and epidermal layers, there appeared to be "new" dermal and epidermal cell formation. Such a finding indicates that the MSC actually differentiate and create epidermal and dermal cells in an organized fashion when used to repair a wound according to this invention.

Example 2

Muscle Stem Cell/SIS Composition

Single layer SIS (Cook Biologic, Inc., Indianapolis, Ind.) was initially incubated in Hank's Buffered Salt Solution for one hour at 37° C. 100,000 late preplate (e.g., PP6), (See, WO 99/56785; and U.S. Pat. No. 6,866,842 and U.S. Pat. No. 7,115,417 to M. Chancellor et al.) rat MSC cells (transduced with a retroviral vector containing Lac Z) were placed onto 1 cm diameter circular SIS to form an MSC-SIS matrix composition. The MSC-SIS matrix was placed into a 24-well culture plate. Different preparations of SIS and MSC were then incubated for 3 days, 1 week, and 2 weeks, respectively, to assess cell viability at 37° C., with daily media changes with Dulbecco's Modified Eagle Media (DMEM, Gibco BRL, Grand Island, N.Y.) supplemented to contain 10% horse serum and 10% fetal bovine serum. At appropriate time intervals, the SIS+MSC matrix combination was harvested and sectioned for staining. At all time intervals, cell viability was evident. The MSC continued to proliferate and form myotubes (evident with Myosin Heavy Chain Staining) at all time intervals. These experiments confirmed that MSC grow on SIS and SIS is not toxic to these cells. Late preplate cells grew in an organized confluent manner.

Example 3

Muscle Stem Cell/Fibrin Glue Composition

Rat MSC from a late preplate (PP6) were obtained using the pre-plate technique (see, WO 99/56785; and U.S. Pat. No. 6,866,842 and U.S. Pat. No. 7,115,417 to M. Chancellor et al.). Fibrin glue was obtained from Baxter Healthcare Corporation (Glendale, Calif.). Fibrin glue is an FDA approved sealant that is composed of human thrombin, calcium chloride, bovine fibrinolysis inhibitor solution, and human sealer protein concentrate. The elements are combined prior to use and injected using a needle syringe. Using 100,000 cells and 0.5 cc of fibrin glue simultaneously, the stem cells and fibrin glue were inoculated onto SIS without using barrier inserts. One day later, the system was harvested and sectioned. After immediate placement of fibrin glue and MSC simultaneously on the SIS, not only did the MSC attach to SIS more quickly, but cell viability was maintained. The fibrin glue did not affect the viability of SIS. This experiment showed the feasibility of using fibrin glue and stem cells to allow for more immediate attachments to matrices and scaffolds.

Example 4

Muscle Stem Cell/Artery Composition

Rat MSC were obtained using the pre-plate technique (see, WO 99/56785; and U.S. Pat. No. 6,866,842 and U.S. Pat. No. 7,115,417 to M. Chancellor et al.) Single layered SIS was seeded with MSC. After a one day incubation in vitro, the MSC/SIS matrix composition was folded into vessel-like lumen. Cell viability was intact after prolonged incubation time (i.e., two weeks) with seeding throughout the vessel lumen.

Example 5

Muscle Stem Cell/Alginate Dressing with Varying Soaking Times

Experiments were performed to assess the effects of soaking MSC in pieces of alginate (1-2 cm$^2$) for 1 minute, 5 minutes, 1 hour, 6 hours, or 12 hours prior to application and use at a tissue or organ site. It was determined that the longer the MSC were soaked in the alginate, the weaker the alginate became, and caused the alginate to dissolve. Weakening of the alginate began as soon as it became hydrated and eventually showed evidence of dissolution within 6 hours of soaking. The results of these studies indicated that immediate or brief soaking with MSC at the point of service was all that was necessary for successful physiological results.

The experiments described in this Example showed that the use of a stem cell concentration of from about 10,000 to 500,000 cells per cm$^2$ of alginate matrix material was sufficient for achieving physiological results. Using the stem cell-biomatrix technique, a large variability in cell concentration and an uneven distribution of cells throughout the matrix material still allowed good physiological results and improvement.

Example 6

Muscle Cells Compared with Fibroblasts Soaked in Alginate

Experiments were conducted to compare the effectiveness of muscle stem cells (MSC) combined with alginate with the effectiveness of fibroblasts combined with alginate in wound healing. A full thickness 1 cm$^2$ wound was made at the dorsum aspect of the upper torso of an anaesthetized rat. All of the experiments were performed by immediately soaking alginate with either the muscle stem cells or fibroblasts. 100,000 late-plate MSC cells (i.e., PP6, see, WO 99/56785; and U.S. Pat. No. 6,866,842 and U.S. Pat. No. 7,115,417 to M. Chancellor et al.) and 100,000 early-plate (i.e., PP1) cells were used with two 1 cm$^2$ pieces of alginate. After two full thickness wounds were created, two, 1 cm$^2$ alginate pieces were soaked with the PP1 cells or the PP6 MSC cells for 5 seconds. This system was then directly placed onto the wound defects and sutured in. The results of these experiments demonstrated that the MSC-alginate combination healed the wound with better cosmoses. In contrast, the fibroblast-alginate composition did not change the healing appearance, but it did heal more quickly than control (alginate alone). Thus, according to the invention, prolonged incubations of cells and the alginate matrix material were not required to effect improved healing of wounds.

Example 7

In Vitro Muscle Stem Cell/SIS Composition

Experiments were performed to assess the adhesion and persistence of late preplate MSC (e.g., PP6, see, WO 99/56785; and U.S. Pat. No. 6,866,842 and U.S. Pat. No. 7,115,417 to M. Chancellor et al.) to an SIS biological scaffold (both 1 and 4 collagen layered SIS). The results demonstrated superior adhesion of the late preplate MSC (i.e., PP6) compared with early preplate cells (i.e., PP1-4).

Using stem cell concentrations of 100,000 per cm$^2$, cell viability was verified after 3 days, 1 week, and 2 weeks for the early and late plate cells. The early plate cells+SIS matrix did not form myotubes well because of the many fibroblasts in the cell population. This created less confluency of the cells on the SIS. The late-plate stem cells (MSC)+SIS proliferated well homogeneously and formed myotubes on the SIS. Cell growth, differentiation into myotubes, and confluency were the desired results achieved by the late plate MSC cells compared with the early plate cells. Increasing the cell count to 1,000,000/cm$^2$ for the early plate cells did not change the results on SIS; however, this increase in cell number for the late-plate MSC cells allowed for the growth of the MSC on SIS in multiple layers.

Example 8

Muscle Stem Cells Alter and Improve SIS Biomechanical Properties

The experiments carried out in this example demonstrated that muscle stem cells (MSC), isolated as described in the aforementioned examples, remodeled SIS and changed the biomechanical properties compared with native SIS. Biomechanical properties of the SIS (and MSC+SIS matrix) were assessed using biaxial testing. For biaxial testing, calculated stresses are applied on all four sides of the SIS using four fine hooks connected to two pulley systems on each side, using procedures known to those having skill in the pertinent art. The stresses applied cause straining to occur within the SIS sample. The data are analyzed and biomechanical properties of the material, such as elasticity, creep, and compliance, can be easily obtained. Upon biaxial testing, native SIS (i.e., SIS with no muscle stem cells) showed decreased horizontal/cross sectional elasticity versus the longitudinal direction. By contrast, a composition containing a combination of MSC and SIS increased the elasticity of the SIS in the horizontal/cross section direction so that it nearly equaled that in the longitudinal direction. The studies were carried out using SIS+MSC cultured for 10 and 20 days in in vitro culture dishes. Thus, these results demonstrate evidence of active remodeling of SIS by MSC.

More particularly, thirty SIS™ sheets (soft-tissue freeze-dried graft, Cook Biotech Incorporated, West Lafayette, Ind.) were prepared for this experiment. The SIS material was kept sealed until testing. Prior to testing, the sheets were cut into the appropriate size to fit into specifically designed sterilized cell culture wells. MSC (1×10$^5$-6) were placed onto the SIS and were fed with culture medium (SMEM). The culture medium was refreshed every 24 hours. The cell culture inserts were incubated at 37° C. for 10 or 20 days. After this time, the specimens were cut into 25 mm square patches and placed into the biaxial mechanical testing setup. (see, e.g., K. L. Billiar and M. S. Sacks, 2000, "Biaxial mechanical properties of the natural and glutaraldehyde treated aortic valve cusp—Part I: Experimental results", *J.*

Biomech. Eng., 122(1):23 and M. S. Sacks, 1999, "A method for planar biaxial mechanical testing that includes in-plane shear", J. Biomech. Eng., 121(5):551-555).

For biaxial mechanical testing, each side of the test specimen was attached to the motor carriages of the biaxial mechanical testing device with sutures looped around two small pulleys on each side of a horizontal common axle, which was connected, in turn, to a vertical pivoting rod, thus allowing near-frictionless rotation in three dimensions. A surgical staple was connected to both ends of each suture line for attachment to the specimen, resulting in a total of four staples per specimen side. Each pulley ensured that the force on each line end was equal; the pivoting rod ensured that the forces were the same on each pair. Small floats were attached to each staple to make the mounted sample neutrally buoyant. Load was monitored in two orthogonal axes by two load cells and the in-plane strain was determined by calculating the centroids of four black markers affixed to the surface of the specimen. The Green's strain (E) along each test axis was calculated from stretch ratio ($\lambda$) using the following equation:

$$E = (\lambda^2 - 1) \div 2$$

Tissue deformations were measured by monitoring the real-time movements of four graphite markers forming a 5-mm square region using real-time video marker tracking. From the marker displacements the 2D in-plane Green's finite strain tensor was computed, where $E_L$ and $E_T$ denote the Green's strain along the longitudinal and transverse directions, respectively. Both the load and deformation in both axes were continuously recorded at 12-15 Hz during testing. All preparations were tested in Hank's buffered saline solution (HBSS) at room temperature. Each test involved 10 contiguous cycles with a period of 20-30 seconds, with a total of seven runs. Testing began with equi-biaxial preconditioning to the maximum stress level. Thereafter, five consecutive tests were conducted, and the axial ratios of the stresses were maintained at values of 0.5:1, 0.75:1, 1:1, 1:0.75, and 1:0.5. These ratios were chosen to determine the mechanical behavior over a wide range of stress states. A final equi-biaxial test was conducted to confirm that the mechanical behavior was not changed during the tests. Total testing time was approximately 60 minutes for each specimen.

The positions of the optical markers at three different stages were recorded during mechanical testing. The first measurement was obtained in the unloaded conditions, with the specimen free-floating in the bath. The second set of marker positions was taken after the sample had attached to the device and a 0.5 gm load was applied to both axes. The preconditioned reference state produced the most stable stress-strain response, and was considered as the most physiological-like state. Thus the marker positions recorded after the first preconditioning run were used for all subsequent strain computations.

The areal strain was used to assess the compliance of the specimen. Areal strain, which is a measure of tissue compliance under biaxial loading, represents the change in tissue area when the tissue is equally loaded along two directions. Areal strain was measured using the following formula:

$$\text{Areal Strain} = (U_1 \times U_2 - 1) \times 100$$

Figure 1:
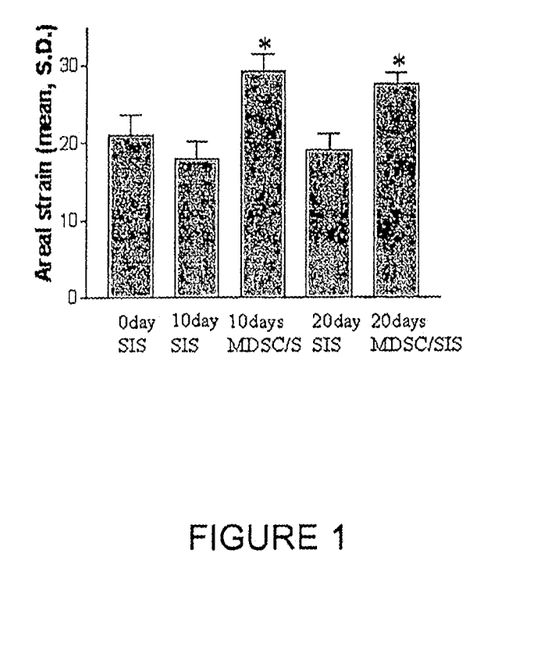
FIG. 1 presents the results of experiments performed to test areal strain of small intestine submucosa (SIS) containing muscle stem cells (MDSC/SIS) compared with non-stem cell containing SIS (control). (Example 8). The mean (±S.D.) areal strain in the control group (n=5) of non-incubated SIS was 20.80±5.9. At 10 days of incubation, the mean (±S.D.) areal strain in MDSC/SIS (29.15±5.4, n=5) was significantly higher (p=0.01) than that of SIS alone (17.98±n=6). Also at 20 days of incubation there were significant differences between SIS alone and MDSC/SIS preparations.

(where, $U_1$: stretch in $X_1$ axis; and $U_2$: stretch in $X_2$ axis) The mean ($\pm$S.D.) areal strain in the control group (n=5) of non-incubated SIS was 20.80$\pm$5.9 (see FIG. 1). At 10 days of incubation, the mean ($\pm$S.D.) areal strain in MSC/SIS (29.15$\pm$5.4, n=5) was significantly higher (p=0.01) than that of SIS alone (17.98$\pm$n=6) (see FIG. 1). Also at 20 days of incubation there were significant differences between SIS alone and the MSC/SIS preparations. These results demonstrate that the MSC/SIS preparations have better compliance properties at 10 and 20 days than SIS alone.

Additionally, when the stretch changes in fiber and non-fiber direction were compared, the increase in stretch change in MDSC/SIS was more prominent in the non-fiber direction than fiber direction axis of the specimens. Thus the biaxial testing results exhibited the classic biological non-linear stress-strain response. The specimens were in a state of nearly pure biaxial strain with negligible shear.

Example 9

Contractility of Muscle Stem Cells (MSC) Incorporated into a SIS Scaffold

Twenty five preparations of MDSC/SIS and twenty five control preparations of SIS only were incubated at 37° C. for 1, 4, or 8 weeks. The specimens were then mounted in a thermally controlled bath of 5 ml at 37° C. in Krebs solution (mmol/L: NaCl, 113; KCl, 4.7; $CaCl_2$, 1.25; $MgSO_4$, 1.2; $NaHCO_3$, 25; $KH_2PO_4$, 1.2 and glucose, 11.5) with a mixture of 95% $O_2$ and 5% $CO_2$. The frequency and amplitude of isometric contractions were measured with strain gauge transducers coupled with a TBM4 strain gauge amplifier and recorded on a computer using a data acquisition program (Windaq, DATAQ Instruments Inc. Akron, Ohio). After 60 minutes of equilibration, electrical field stimuli (10 Hz, 150 volt, 0.5 ms, 60 sec) were applied in the bath. Pharmacological evaluations were performed with succinylcholine (S-Chol), (4, 10 and 20 μM); carbachol (10 and 20 μM); KCl, (7%, 1M); $Ca^{++}$-free Krebs solution with EGTA (20 μM); or distilled water, were each added to the bath sequentially at 30 minute intervals. The frequency, amplitude, and pattern of contraction of the specimens were compared among the different groups.

Figure 2:
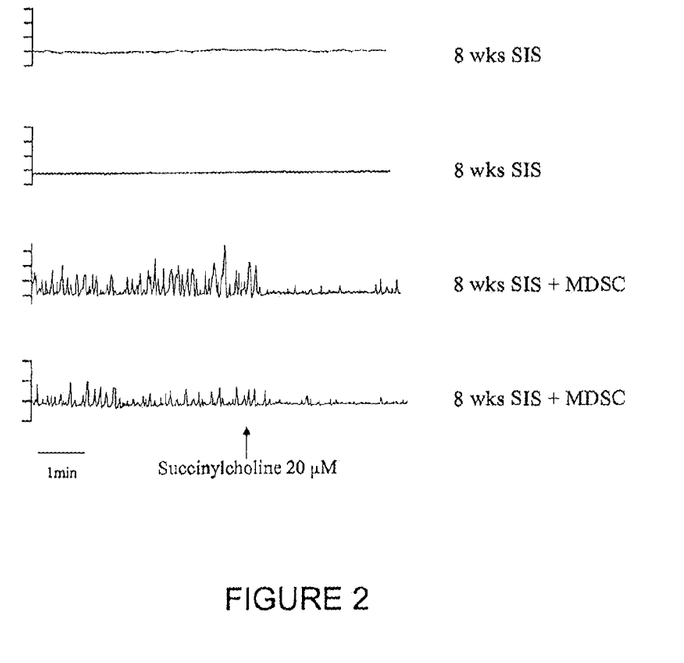

All MDSC/SIS specimens were curved in shape, thus suggesting tonic contractile activity. In contrast, the specimens having SIS alone did not have a curved shape (FIG. 2). All of the SIS only control groups of the 1 (n=11), 4 (n=6), and 8-week (n=8) specimens did not show any activity in the bath. In the 4-week (5 of 6 specimens) and 8-week cultures (8 of 8 specimens) of MDSC/SIS preparations, spontaneous contractile activity was observed. However, in the 1-week MDSC/SIS cultures no spontaneous contractility was observed (0 of 11 specimens).

In the 8-week MDSC/SIS preparations, the frequency and amplitude of spontaneous contractile activity (SCA) were decreased in all (8 of 8) specimens by S-Chol (10 μM) and were blocked in 5 of 8 specimens after administration of S-Chol (20 μM). In the 4-week MDSC/SIS preparations, the frequency and amplitude of SCA were decreased in 2 of 5 specimens by S-Chol (10 μM) and were decreased in 5 of 5 specimens and blocked in 2 of 5 specimens by S-Chol (20 μM). The suppressant effects observed were reversible after washout of the drug. S-Chol (4 μM) did not alter the frequency, amplitude, or pattern of spontaneous activity of any of the preparations.

In all of the MDSC/SIS specimens, spontaneous contractile activity was blocked by both $Ca^{++}$-free Krebs solution with EGTA (200 μM) and distilled water. However, electrical field stimulation, carbachol, and KCl did not alter the frequency, amplitude, and pattern of the spontaneous contractile activity in MDSC/SIS specimens. Accordingly, the 8-week results suggest that the MDSC/SIS scaffold is able to generate contractile activity which is Ca++-dependent and modulated by nicotinic receptors. (FIG. 2).

Example 10

Effectiveness of MSC/SIS Suburethral Sling Placement in a Rat

To evaluate the effectiveness of the MDSC/SIS suburethral sling placement in a female rat, the bilateral proximal sciatic nerve transection (PSNT) model of stress urinary incontinence (SUI) was used. Both bilateral pudendal nerve transection, or pudendal nerve crush, result in alterations in behavioral voiding patterns and significant histological changes of urethral striated muscle atrophy. In initial studies for SIS sling placement, more proximal nerve transection at the level of the sciatic nerve (before the branching of the pudendal nerves) was used, combined with the vertical tilt table and intravesical pressure clamp method of leak point pressure (LPP) testing.

Five halothane anesthetized rats underwent bilateral sciatic nerve transection and periurethral sling placement using a SIS/MDSC patch. The sling comprised an SIS strip with dimensions of 14 mm in length and 3 mm in width. This sling was placed posterior to the urethra via a transabdominal approach, and was sutured bilaterally into the pubic bone using 4.0 prolene, 6 mm lateral to the pubic symphysis. An intraurethral catheter (PE20) was inserted prior to tying the sling sutures in place to ensure that the sling would not produce obstruction. Care was taken not alter the natural bladder/urethral angle. Sham rats (n=2) underwent bilateral proximal sciatic nerve transection and identical periurethral dissection without SIS/MDSC sling placement. The rats were subsequently monitored for signs of urinary retention and given antibiotic therapy once every 3 days.

Two weeks following surgery, the rats underwent leak point pressure (LPP) testing using the vertical tilt/intravesical pressure clamp method. (see, O. Matthew et al., 2000, "Creation of a new stess incontinence model in the rat by using vertical tilt table and surgical or pharmacological manipulation of internal and external sphincter activity with measurement of leak point pressure (LPP)", 2000 Annual Meeting of the AUA, *J. Urol.*, 163:76). Control rats (n=5) also underwent the same LPP testing, but without prior treatment. It was determined that LPPs in PSNT rats with slings were not significantly different from those of control rats (51.23±1.60 versus 46.11±1.83, respectively). Importantly, no PSNT-sling rat demonstrated signs of urinary retention. (28.6±0.8 cm $H_2O$ for 1 week LPP in denervated rats). Thus, these findings demonstrated that the SIS/MDSC sling restored LPP in the PSNT rat model of SUI to nearly that of LPP in normal control rats. MDSC/SIS according to the present invention restores muscular function and innervation to the damaged sphincter. It is therefore an added advantage of this invention not only to prepare a scaffold with MDC, but also to achieve a type of 3-dimensional muscle replacement for in vivo use in tissue and organ repair using the MDSC/SIS that behaves as a muscle, including innervation and neuromuscular receptors.

All patent applications, published applications, patents, texts, and literature references cited in this specification are hereby incorporated herein by reference in their entirety to more fully describe the state of the art to which the present invention pertains.

As various changes can be made in the above methods and compositions without departing from the scope and spirit of the invention as described, it is intended that all subject matter contained in the above description, shown in the accompanying drawings, or defined in the appended claims be interpreted as illustrative, and not in a limiting sense.

The invention claimed is:

1. A method of repairing and/or patching a blood vessel comprising seeding a single layer of small intestine submucosa (SIS) with muscle-derived progenitor cells (MSC) to form a MSC/SIS matrix; wherein the MSC/SIS matrix is formed by a method comprising: a) admixing a preparation comprising the MSC with the SIS to form a stem cell matrix dressing; b) incubating the stem cell matrix dressing in vitro for 5 seconds to about less than 3 hours, thereby forming the MSC/SIS matrix; and c) folding the MSC/SIS matrix into a vessel-like lumen around the blood vessel, thereby repairing and/or patching the blood vessel.

2. The method of claim 1, wherein the MSC are inoculated onto SIS simultaneously with fibrin glue to form the MSC/SIS matrix.

3. The method of claim 1, wherein the MSC are autologous or allogeneic to a recipient in need of the vessel like lumen.

4. The method of claim 3, wherein allogeneic cells are from a donor with class I and class II histocompatibility antigen closest matched with the recipient.

5. The method of claim 4, wherein the recipient is on immunosuppressive or immunomodulatory therapy started before, during, and/or after the matrix is applied or introduced into the recipient.

6. The method of claim 5, wherein the immunosuppressive drug is cyclosporine A.

7. A method of repairing urethral muscle in a subject in need thereof comprising: a) admixing a preparation comprising muscle-derived progenitor cells (MSCs) with a small intestine submucosa (SIS) to form a stem cell matrix dressing; and b) incubating the stem cell matrix dressing in vitro for 5 seconds to about less than 3 hours, thereby forming the MSC/SIS matrix; c) supporting the urethral muscle of the subject with the MSC/SIS matrix, wherein the MSC/SIS matrix repairs the urethral muscle.

8. The method of claim 7, wherein the MSC/SIS matrix is contractible.

9. The method of claim 7, wherein the MSC are inoculated onto SIS simultaneously with fibrin glue to form the MSC/SIS matrix.

10. The method of claim 7, wherein the MSC are autologous or allogeneic to a recipient in need of the MSC/SIS matrix.

11. The method according to claim 1, wherein the stem cell matrix dressing is incubated in vitro for less than about 1 hour.

12. The method according to claim 1, wherein the stem cell matrix dressing is incubated in vitro for less than about 30 minutes.

13. The method according to claim 7, wherein the stem cell matrix dressing is incubated in vitro for less than about 1 hour.

14. The method according to claim 7, wherein the stem cell matrix dressing is incubated in vitro for less than about 30 minutes.

* * * * *

UNITED STATES PATENT AND TRADEMARK OFFICE
CERTIFICATE OF CORRECTION

PATENT NO. : 9,744,267 B2  
APPLICATION NO. : 14/972402  
DATED : August 29, 2017  
INVENTOR(S) : Michael B. Chancellor et al.

Page 1 of 1

It is certified that error appears in the above-identified patent and that said Letters Patent is hereby corrected as shown below:

In the Specification

At Column 1, Lines 18-20, delete:
"This invention was made with Government support under Grant No. DK55387 awarded by the National Institutes of Health. The Government has certain rights in this invention."

And replace with:
-- This invention was made with government support under grant number DK055387 awarded by the National Institutes of Health. The government has certain rights in the invention. --

Signed and Sealed this
Twenty-ninth Day of October, 2019

Andrei Iancu
*Director of the United States Patent and Trademark Office*